(12) United States Patent
Carlo et al.

(10) Patent No.: US 12,329,393 B2
(45) Date of Patent: Jun. 17, 2025

(54) TARGETING GUIDE

(71) Applicant: WRIGHT MEDICAL TECHNOLOGY, INC., Memphis, TN (US)

(72) Inventors: Robert Michael Carlo, Lakeland, TN (US); George Matthew Awtrey, Bartlett, TN (US)

(73) Assignee: WRIGHT MEDICAL TECHNOLOGY, INC., Memphis, TN (US)

( * ) Notice: Subject to any disclaimer, the term of this patent is extended or adjusted under 35 U.S.C. 154(b) by 471 days.

(21) Appl. No.: 17/814,606

(22) Filed: Jul. 25, 2022

(65) Prior Publication Data

US 2023/0052337 A1 Feb. 16, 2023

Related U.S. Application Data

(60) Provisional application No. 63/231,449, filed on Aug. 10, 2021.

(51) Int. Cl.
| | | |
|---|---|---|
| *A61B 17/17* | (2006.01) | |
| *A61B 17/16* | (2006.01) | |
| *A61B 90/50* | (2016.01) | |
| *A61B 17/56* | (2006.01) | |

(52) U.S. Cl.
CPC ...... *A61B 17/1728* (2013.01); *A61B 17/1615* (2013.01); *A61B 17/1633* (2013.01); *A61B 90/50* (2016.02); *A61B 2017/565* (2013.01)

(58) Field of Classification Search
CPC .. A61B 2090/506; A61B 2017/320052; A61B 2017/3405; A61B 17/90; A61B 17/1725; A61B 90/11; A61B 17/1775; A61B 2017/565

See application file for complete search history.

(56) References Cited

U.S. PATENT DOCUMENTS

| | | | | |
|---|---|---|---|---|
| 4,444,180 A | * | 4/1984 | Schneider | A61B 17/1714 606/96 |
| 4,708,139 A | * | 11/1987 | Dunbar, IV | A61B 17/1764 D24/140 |
| 4,739,751 A | * | 4/1988 | Sapega | A61B 17/1764 606/88 |
| 4,813,407 A | * | 3/1989 | Vogen | A61B 17/29 606/86 R |
| 5,269,305 A | * | 12/1993 | Corol | A61B 90/11 378/20 |
| 5,397,323 A | * | 3/1995 | Taylor | A61B 34/71 901/41 |
| 5,584,839 A | * | 12/1996 | Gieringer | A61B 17/1778 606/103 |
| 6,488,030 B1 | | 12/2002 | Wardle et al. | |
| 6,702,805 B1 | * | 3/2004 | Stuart | A61B 34/71 606/1 |
| 7,204,168 B2 | * | 4/2007 | Najafi | A61B 34/70 74/471 XY |
| 8,551,123 B2 | * | 10/2013 | Pandya | A61B 17/1684 606/148 |
| D708,259 S | * | 7/2014 | Fagan | D19/108 |

(Continued)

*Primary Examiner* — David W Bates
(74) *Attorney, Agent, or Firm* — DUANE MORRIS LLP

(57) ABSTRACT

Disclosed are bone screw drill targeting guides and methods for using such targeting guides that are useful in surgical procedures for correcting hallux valgus deformity.

15 Claims, 5 Drawing Sheets

(56) References Cited

U.S. PATENT DOCUMENTS

| | | | | |
|---|---|---|---|---|
| 10,154,868 | B2* | 12/2018 | Fallin | A61B 17/8861 |
| 11,298,143 | B2* | 4/2022 | Santangelo | A61B 50/20 |
| 11,517,348 | B2* | 12/2022 | Abboud | A61B 90/57 |
| 2003/0109825 | A1* | 6/2003 | Loser | A61B 17/3403 604/131 |
| 2004/0193172 | A1* | 9/2004 | Ross | A61B 17/1778 606/96 |
| 2012/0118088 | A1* | 5/2012 | Smith | A61B 90/57 384/15 |
| 2015/0157466 | A1* | 6/2015 | Crawford | A61B 17/1757 623/17.16 |
| 2015/0157468 | A1* | 6/2015 | Wakayama | A61B 90/11 606/86 R |
| 2016/0367270 | A1* | 12/2016 | Garlock | A61B 17/1739 |
| 2017/0007335 | A1* | 1/2017 | Popovic | B25J 19/00 |
| 2017/0238997 | A1* | 8/2017 | Pandya | A61B 34/20 |
| 2018/0296244 | A1* | 10/2018 | Kim | A61B 17/3472 |
| 2020/0113633 | A1* | 4/2020 | Pandya | A61B 90/11 |
| 2020/0375436 | A1* | 12/2020 | Kielack | A61B 90/50 |
| 2020/0375668 | A1* | 12/2020 | Pandya | A61B 34/20 |
| 2021/0015503 | A1* | 1/2021 | Arciero | A61B 17/1796 |
| 2021/0113223 | A1* | 4/2021 | Schaumann | A61B 17/56 |

* cited by examiner

TARGETING GUIDE

CROSS-REFERENCE TO RELATED APPLICATION

This application claims priority under 35 U.S.C. § 119 (e) to U.S. Provisional Application No. 63/231,449, filed on Aug. 10, 2021, the entire contents of which are incorporated herein by reference.

FIELD OF DISCLOSURE

The present disclosure relates to an instrument for guiding a screw or a wire through bone or bones toward a desired target point that can be used in surgical procedures. for correcting hallux valgus deformity.

BACKGROUND

Guiding a screw or a wire through a bone or multiple bones and/or joints is difficult especially for less experienced surgeons because in many procedures, the target point for the screw or wire is inside a bone and thus not visible. For example, during a minimally invasive surgical procedures such as Minimally Invasive Chevron and Akin osteotomy (MICA) procedure for correcting hallux valgus deformity, a Chevron osteotomy is made in the first metatarsal bone separating the head portion of the first metatarsal from the remainder of the metatarsal. The metatarsal head is then shifted laterally and fixed with two screws. K-wires are traditionally used to hold the metatarsal head at the intended translated position during the subsequent screw fixation procedure. Achieving the desired k-wire trajectory can be difficult. Therefore, a guiding instrument for setting the trajectory of the K-wire in such instance is desired.

SUMMARY

Disclosed herein is a targeting guide instrument that is configured to allow a surgeon to place a guide wire or a screw at any orientation and it will always pass through a predetermined location in relation to the guide instrument. Thus, by matching the predetermined location of the guide instrument to be the desired target point inside a bone, for example, the surgeon can insert a guide wire or a screw to that target point guided by the guide instrument. The disclosed targeting guide can be useful for placing a guide wire, such as a K-wire, or a screw through two adjacent bone pieces. The two adjacent bone pieces can be two portions of a bone or two adjacent bones.

The targeting guide comprises: a first guide sleeve defining a first longitudinal axis; a second guide sleeve defining a second longitudinal axis; an articulating arm connecting the first guide sleeve and the second guide sleeve; where the first longitudinal axis and the second longitudinal axis intersect at an intersection point in space and form an intersecting angle, the intersection point being located at a first distance from the first guide sleeve and at a second distance from the second guide sleeve; where manipulating the articulating arm changes the intersecting angle while maintaining the same intersection point; and where the articulating arm is configured to be able to change the first distance.

A surgical instrument kit is also disclosed, where the kit comprises at least one guide wire and a targeting guide of the present disclosure. A surgical instrument kit comprising at least one guide wire, at least one drill bit, and a targeting guide of the present disclosure is also disclosed.

BRIEF DESCRIPTION OF THE DRAWINGS

The inventive concepts of the present disclosure will be described in more detail in conjunction with the following drawing figures. The structures in the drawing figures are illustrated schematically and are not intended to show actual dimensions.

DETAILED DESCRIPTION

Figure 1:
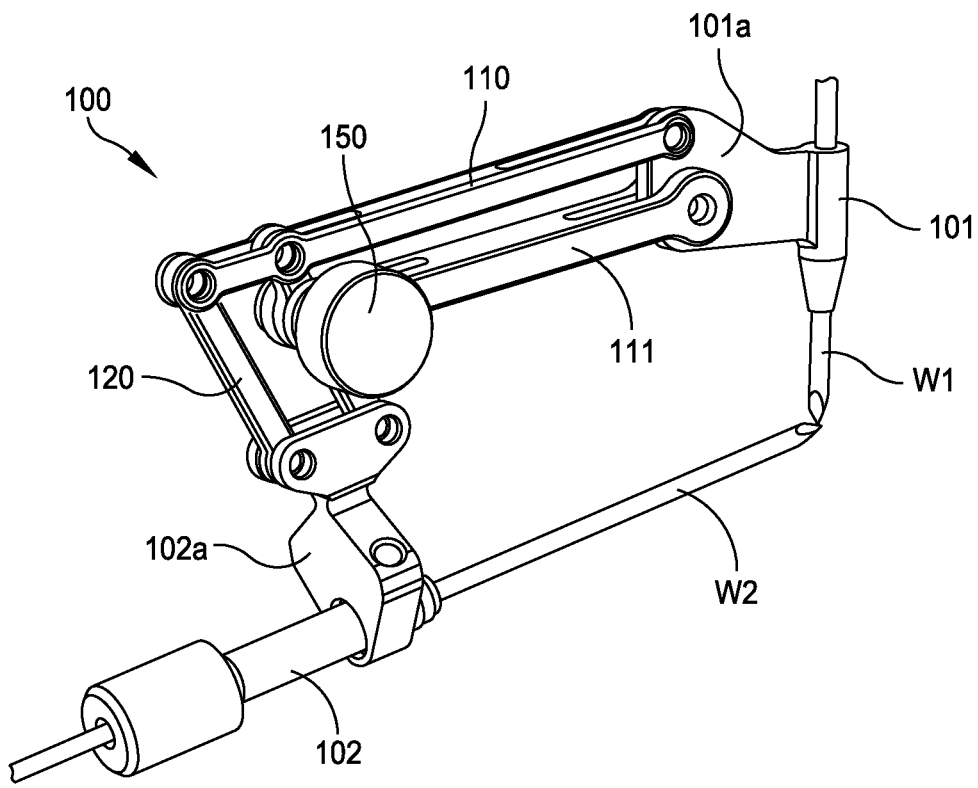
FIG. 1 is an isometric view of the targeting guide of the present disclosure.
Figure 2:
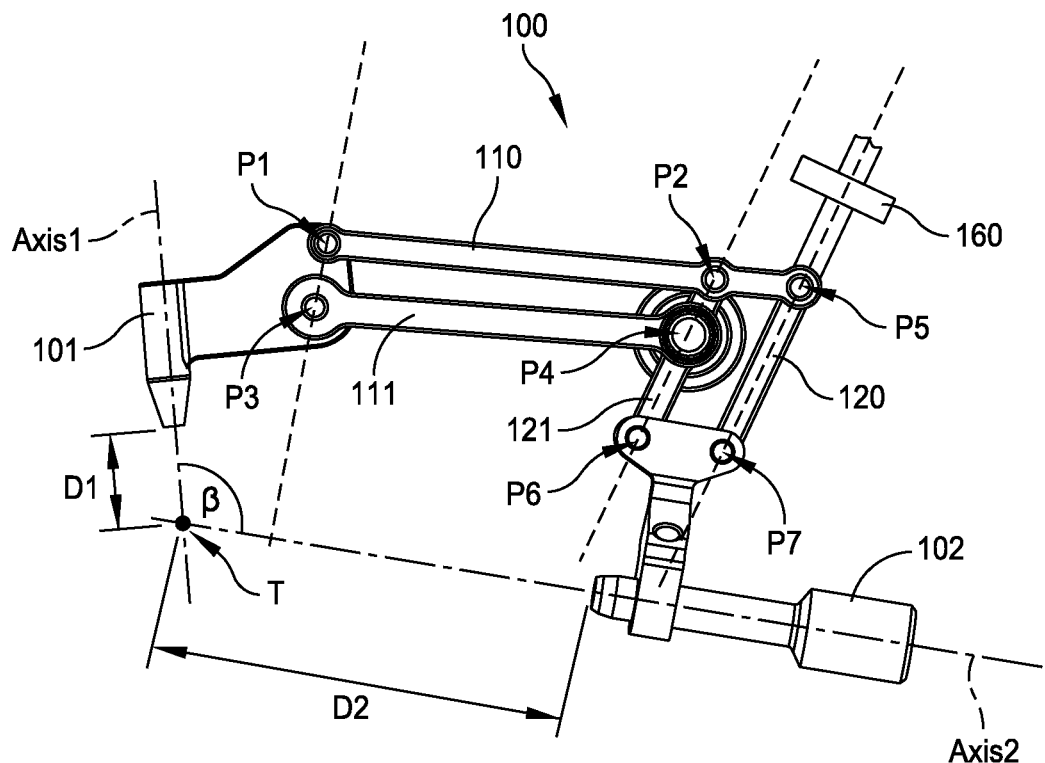
FIG. 2 is plan view of the targeting guide of FIG. 1.

This description of the exemplary embodiments is intended to be read in connection with the accompanying drawings, which are to be considered part of the entire written description. The drawing figures are not necessarily to scale and certain features may be shown exaggerated in scale or in somewhat schematic form in the interest of clarity and conciseness. In the description, relative terms such as "horizontal," "vertical," "up," "down," "top" and "bottom" as well as derivatives thereof (e.g., "horizontally," "downwardly," "upwardly," etc.) should be construed to refer to the orientation as then described or as shown in the drawing figure under discussion. These relative terms are for convenience of description and normally are not intended to require a particular orientation. Terms including "inwardly" versus "outwardly," "longitudinal" versus "lateral" and the like are to be interpreted relative to one another or relative to an axis of elongation, or an axis or center of rotation, as appropriate. Terms concerning attachments, coupling and the like, such as "connected" and "interconnected," refer to a relationship wherein structures are secured or attached to one another either directly or indirectly through intervening structures, as well as both movable or rigid attachments or relationships, unless expressly described otherwise. When only a single machine is illustrated, the term "machine" shall also be taken to include any collection of machines that individually or jointly execute a set (or multiple sets) of instructions to perform any one or more of the methodologies discussed herein. The term "operatively connected" is such an attachment, coupling or connection that allows the pertinent structures to operate as intended by virtue of that relationship. In the claims, means-plus-function clauses, if used, are intended to cover the structures described, suggested, or rendered obvious by the written description or drawings for performing the recited function, including not only structural equivalents but also equivalent structures.

Referring to FIGS. 1 through 5, a targeting guide 100 is disclosed that is configured to allow a surgeon to place a guide wire W2 or a screw at any orientation that will always pass through a predetermined location, a target location, in relation to the targeting guide 100. The targeting guide 100 comprises a first guide sleeve 101 defining a first longitudinal axis Axis1, a second guide sleeve 102 defining a second longitudinal axis Axis2, and an articulating arm connecting the first guide sleeve 101 and the second guide sleeve 102.

The first longitudinal axis Axis1 and the second longitudinal axis Axis2 intersect at an intersection point T, that is the predetermined location in space, so as to form an intersecting angle β. The intersection point T is located at a first distance D1 (labeled in FIG. 2) from the first guide sleeve 101 and at a second distance D2 (labeled in FIG. 2) from the second guide sleeve 102. Flexing the articulating arm changes the intersecting angle β while maintaining the intersection point T at the first distance D1 from the first guide sleeve 101 and at the second distance D2 from the second guide sleeve 102. In other words, the intersection point T remains at the same point in space relative to the first guide sleeve 101 and the second guide sleeve 102 while the articulating arm is flexed to change the intersecting angle β. This is graphically explained in FIG. 5. The dotted lines Axis2a, Axis2b, Axis2c, and Axis2d illustrate some examples of different orientations that the second longitudinal axis Axis2 can be placed by flexing and manipulating the articulating arm. As can be seen, no matter what orientation the second longitudinal axis Axis2 is in, it always intersects the first longitudinal axis Axis1 at the intersection point T.

Figure 7:
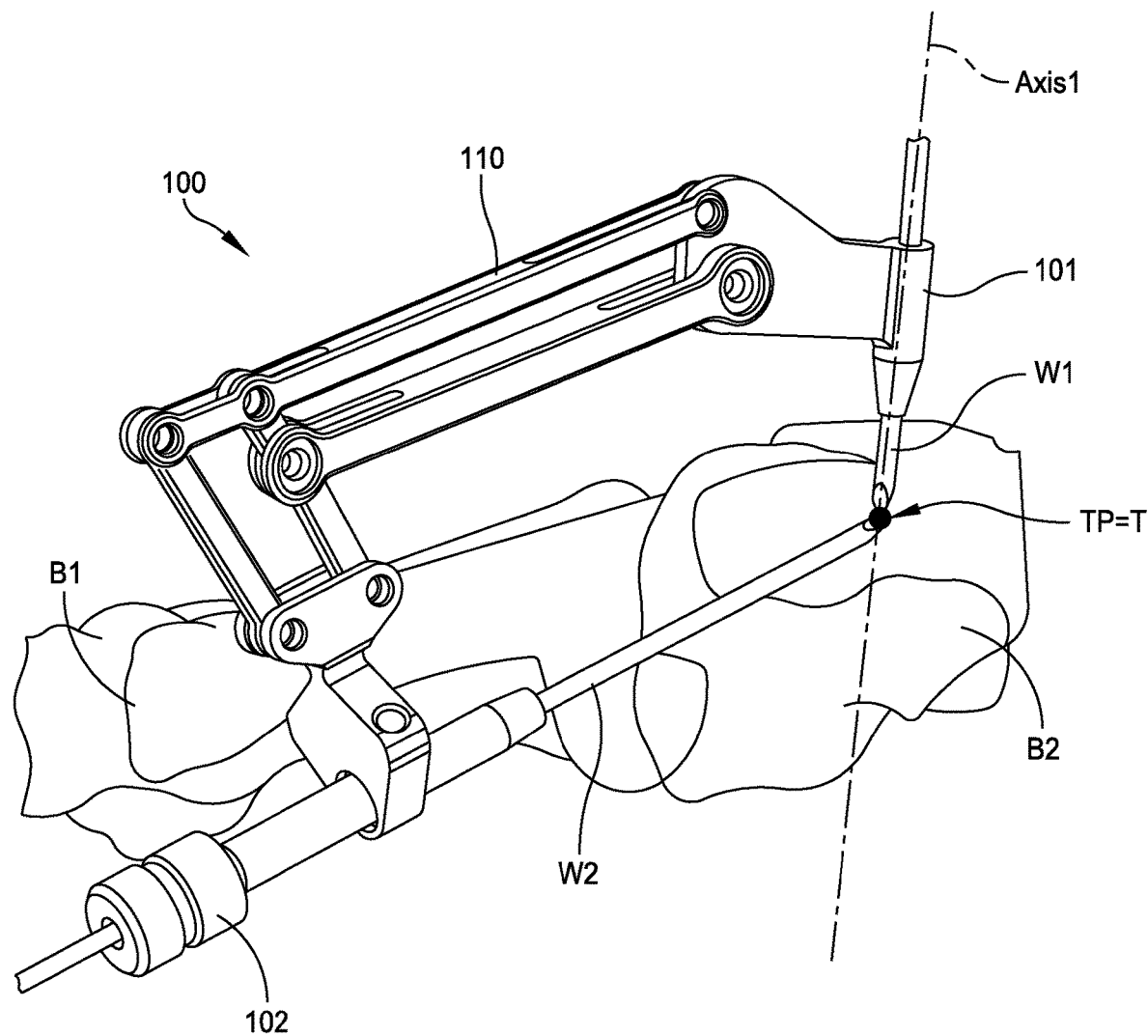
FIG. 7 is an illustration showing the targeting guide of the present disclosure where the second guide wire W2 has been shot through the first and second bone pieces B1, B2.

Referring to FIG. 7, this feature of the targeting guide 100 is useful in situations where a guide wire W2 needs to be placed through a first bone piece B1 and into a second bone piece B2 toward a predetermined target point TP where the target point TP is inside the second bone piece B2 and is not visible to the surgeon. Because the second guide sleeve 102 always points toward the intersection point T, which is located along the first longitudinal axis Axis1 at the first distance D1 from the tip of the first guide sleeve 101, by placing the first guide sleeve 101 against the second bone piece B2 so that the first longitudinal axis Axis1 goes through the predetermined target point TP and that the tip of the first guide sleeve 101 is at the first distance D1 from the target point TP, the intersection point T of the targeting guide 100 and the target point TP in the second bone B2 will be the same point in space. Then the guide wire W2 extending through the second guide sleeve 102 will always be aimed at the predetermined target point TP no matter the angular orientation the second guide sleeve 102. This ensures that the surgeon will always hit the predetermined target point TP with the guide wire W2.

Figure 6:
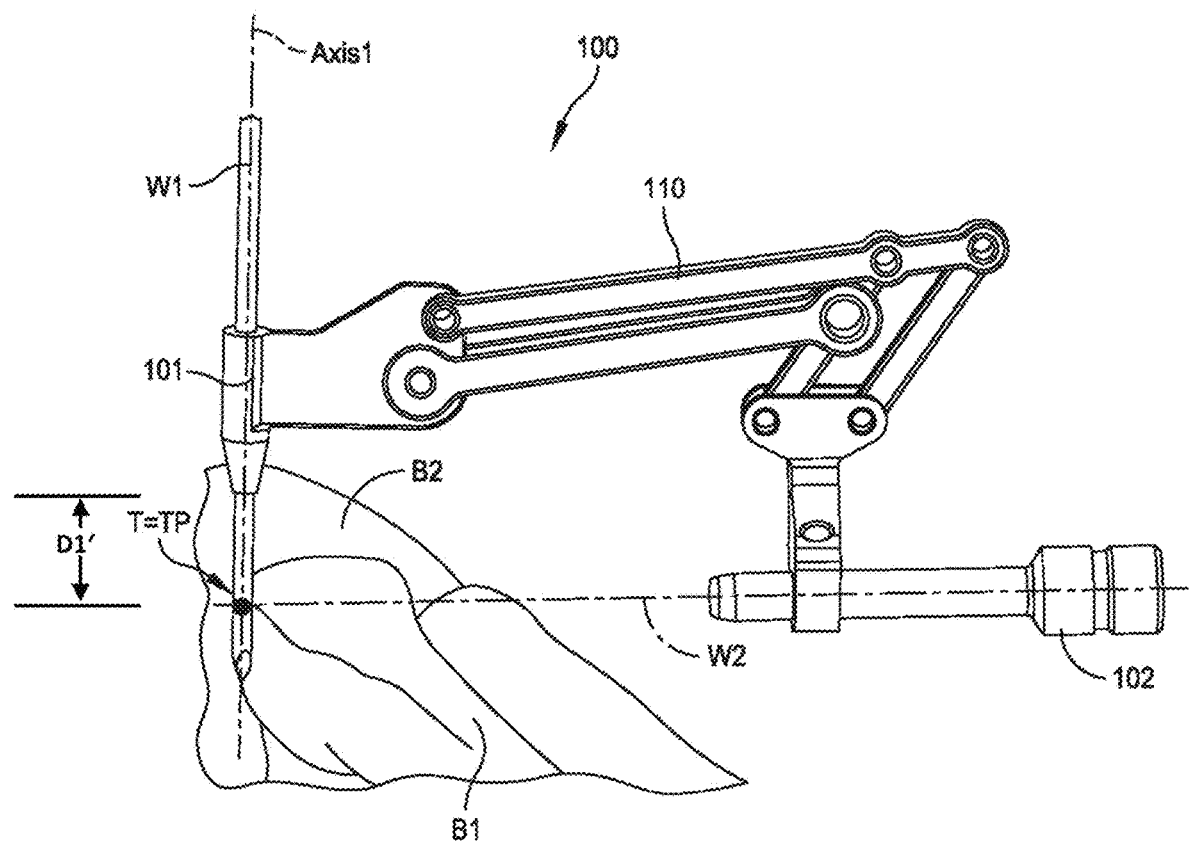
FIG. 6 is an illustration showing the targeting guide of the present disclosure where the first guide sleeve has been slipped over the first guide wire W1.

Additionally, the articulating arm is configured to be able to change the first distance D1 to D1' as shown in FIG. 6. This adjustability allows one to change the location of the intersection point T with respect to the first guide sleeve 101.

In some embodiments of the targeting guide 100, the articulating arm comprises a first pair of linkages 110, 111 that are arranged parallel to each other and a second pair of linkages 120, 121 that are also arranged parallel to each other. Each of the linkages 110, 111 in the first pair have a first end and a second end, the first ends being hingeably connected to the first guide sleeve 101 at respective first hinge points P1, P3. Each of the linkages 120, 121 in the second pair have a first end and a second end, the first end being hingeably connected to the second guide sleeve 102 at respective second hinge points P6, P7. The second ends of the linkages 110, 111 in the first pair are arranged and hingeably connected to the second ends of the linkages 120, 121 in the second pair to form a pair of nested hinged joints that allow the two pairs of linkages to flex and form a flex angle θ of less than 180 degrees while keeping the two linkages in each pair to remain parallel to each other. The first of the two nested hinged joints are formed by one linkage 110, 120 from each pair being connected. The second of the two nested hinged joints are formed by another linkage 111, 121 from each pair being connected.

Figure 3:
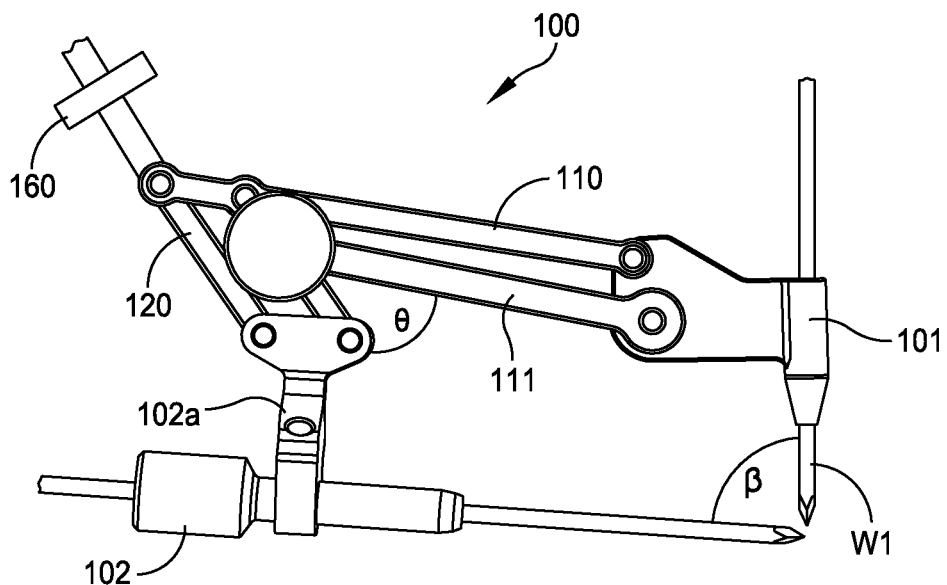
FIGS. 3-5 are side views of the targeting guide of the present disclosure.
Figure 4:
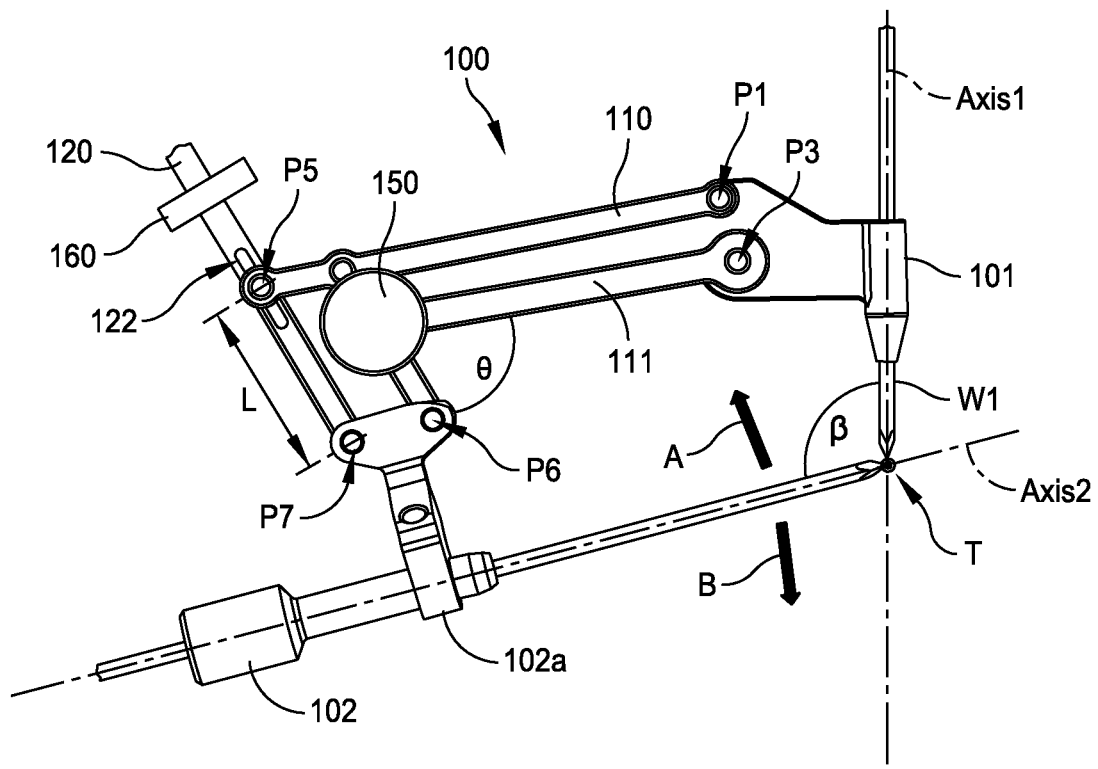
Figure 5:
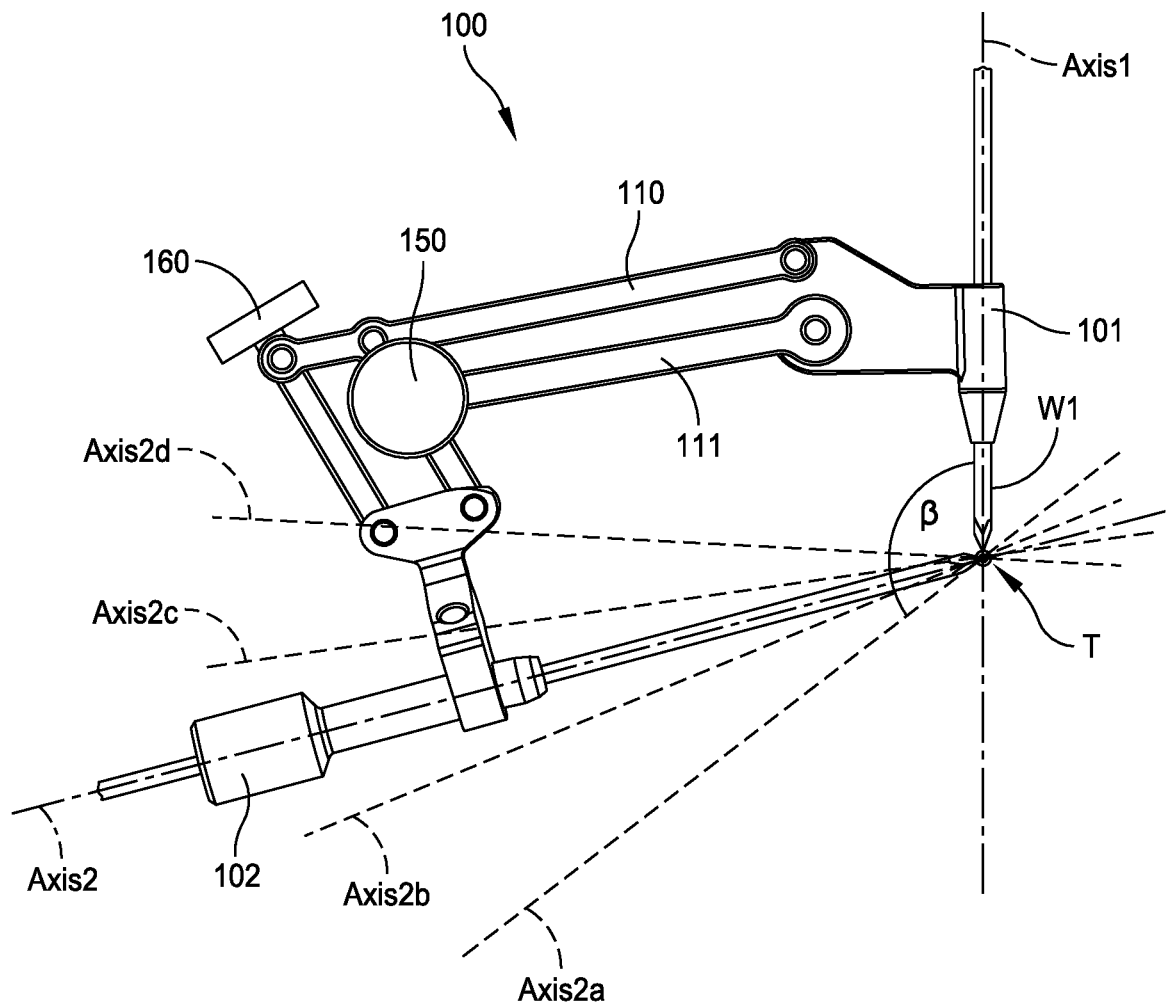

Referring to FIGS. 3-4, the first of the pair of nested hinged joints formed by the linkages 110 and 120 is referred to as an outer joint and the second of the pair of hinged joints formed by the two linkages 111 and 121 is referred to as an inner joint. The hinged joint formed by the linkages 111 and 121 is referred to as an inner joint because that hinged joint is nested inside the hinged joint formed by the two linkages 110 and 120. The hinged joint formed by the linkages 110 and 120 is referred to as an outer joint because that hinged joint is outside the hinged joint formed by the two linkages 111 and 121. Because the first pair of linkages 110 and 111 are parallel and the second pair of linkages 120 and 121 are parallel, the two nested hinged joints form the same flex angle θ.

In some embodiments of the targeting guide 100, the linkage 120 forming the outer joint is configured so that the length L (labeled in FIG. 4) between the nested hinge joint P5 and the second hinge point P7 can be adjusted to change the first distance D1 to D1' (FIG. 6). The linkage 120 can be provided with a slot 122 in which the nested hinge joint P5 can slide to increase or decrease the length L. The sliding arrangement between the nested hinge joint P5 and the linkage 120 can be configured so that a thumbwheel 160 can be used to make the nested hinge joint P5 slide within the slot 122 and adjust the length L. For example, making the length L shorter will cause the second guide sleeve holder 102a to pivot about the hinge joints P6 and P7 and change the attitude of the second guide sleeve 102 so that the second longitudinal axis Axis2 defined by the second guide sleeve 102 to tilt in the direction of the arrow B shown in FIG. 4. This will move the intersection point T to move away from the first guide sleeve 101 thus increasing the first distance D1 to D1' and decrease the intersecting angle β. On the other hand, making the length L longer will cause the second guide sleeve holder 102a to pivot about the hinge joints P6 and P7 in the opposite direction and change the attitude of the second guide sleeve 102 so that the second longitudinal axis Axis2 defined by the second guide sleeve 102 to tilt in the direction of the arrow A shown in FIG. 4. This will move the intersection point T to move toward the first guide sleeve 101, thus, decreasing the first distance D1 and increase the intersecting angle β. This feature can be used to adjust the location of the predetermined target point TP inside the target bone piece.

Referring to FIG. 1, in some embodiments of the targeting guide 100, the first guide sleeve 101 is configured to receive a surgical guide wire W1. In some embodiments, the second guide sleeve 102 is configured to receive a surgical guide wire.

In some embodiments of the targeting guide 100, the first guide sleeve 101 is configured to receive and guide a drill bit. In some embodiments, the second guide sleeve 102 is configured to receive and guide a drill bit.

The associated surgical method of using the targeting guide 100 will now be described. First, a guide wire W1, such as a K-wire, is placed into the bone piece B2 at a location so that the guide wire W1 is either pointing at the predetermined target point TP inside the second bone piece B2 or the guide wire W1 is extending through the predetermined target point TP. In other words the predetermined target point TP is axially aligned with the guide wire W1 so that the predetermined target point TP is somewhere along the longitudinal axis of the guide wire W1.

Then, the first guide sleeve 101 is placed over the guide wire W1 and positioned along the guide wire W1 so that the intersection point T of the targeting guide 100 coincides with the predetermined target point TP. As described above the intersection point T of the targeting guide 100 is located along the first longitudinal axis Axis1 of the first guide sleeve 101 at the first distance D1 from the tip of the first guide sleeve 101. At this point the arrangement looks something like shown in FIG. 6.

Next, the targeting guide 100 is adjusted so that the second guide sleeve 102 is in a position with an orientation that represents the orientation of the bone screw that the surgeon would like to insert through the first bone piece B1 and into the second bone piece B2. Once the second guide sleeve 102 is in position, a second guide wire W2 can be shot through the second guide sleeve 102 toward the intersection point T which will be at the predetermined target point TP.

Once the guide wire W2 is placed in position, the targeting guide 100 and the first guide wire W1 can be removed and a cannulated drill bit can be slipped over the guide wire W2 and used to drill a hole into the bone pieces B1, B2. Alternatively, a cannulated bone screw can be slipped over the guide wire W2 and screwed into the bone pieces B1, B2.

In some other embodiments, after the second guide sleeve 102 is in position, rather than shooting the second guide wire W2 through the second guide sleeve 102, a pilot hole for a screw can be drilled through the bone pieces B1, B2 using the second guide sleeve 102 as a drill guide. A bone screw can then be threaded into the pilot hole to secure the two bone pieces B1, B2 together. Alternatively, without drilling a pilot hole, a self-tapping bone screw can be inserted through the second guide sleeve 102 and driven into the bone pieces B1, B2.

The targeting guide 100 and the associated method can be applied to such procedure as Minimally Invasive Chevron and Akin osteotomy (MICA) procedure for correcting hallux valgus deformity where the head portion and the reminder portion of the first metatarsal bone after the Chevron osteotomy are the second bone piece B2 and the first bone piece B1, respectively. After the metatarsal head is shifted laterally, the targeting guide 100 of the present disclosure can be used to fix the two bone pieces using two screws.

According to an aspect of the present disclosure, a surgical instrument kit is also disclosed, where the kit comprises at least one guide wire and a targeting guide of the present disclosure. A surgical instrument kit comprising at least one guide wire, at least one drill bit, and a targeting guide of the present disclosure is also disclosed.

Although the devices, kits, systems, and methods have been described in terms of exemplary embodiments, they are not limited thereto. Rather, the appended claims should be construed broadly, to include other variants and embodiments of the devices, kits, systems, and methods, which may be made by those skilled in the art without departing from the scope and range of equivalents of the devices, kits, systems, and methods.

We claim:

1. A targeting guide comprising:
a first guide sleeve defining a first longitudinal axis;
a second guide sleeve defining a second longitudinal axis;
an articulating arm connecting the first guide sleeve and the second guide sleeve that comprises a first pair of parallel linkages and a second pair of parallel linkages,
wherein each of the linkages in the first pair having a first end and a second end, the first end being hingeably connected to the first guide sleeve at a first hinge point,
wherein each of the linkages in the second pair having a first end and a second end, the first end being hingeably connected to the second guide sleeve at a second hinge point,
wherein the second ends of the linkages in the first pair are arranged and hingeably connected to the second ends of the linkages in the second pair to form a pair of nested hinged joints that allow the two pairs of linkages to flex and form a flex angle of less than 180 degrees while keeping the two linkages in each pair to remain parallel to each other,
wherein one linkage from each pair are connected to form a first of the pair of nested hinged joints and another linkage from each pair are connected to form a second of the pair of nested hinged joints,
wherein the first of the pair of nested hinged joints is an inner joint and the second of the pair of nested hinged joints is an outer joint configured so that its length between the nested hinged joint, it forms, and the second hinge point can be adjusted to change the first distance;
wherein the first longitudinal axis and the second longitudinal axis intersect at an intersection point in space and form an intersecting angle, the intersection point being located at a first distance from the first guide sleeve and at a second distance from the second guide sleeve;
wherein flexing the articulating arm changes the intersecting angle while maintaining the same intersection point; and
wherein the articulating arm is configured to be able to change the first distance.

2. The targeting guide of claim 1, wherein the first guide sleeve is configured to receive a surgical guide wire.

3. The targeting guide of claim 1, wherein the first guide sleeve is configured to receive a surgical guide wire.

4. The targeting guide of claim 1, wherein the second guide sleeve is configured to receive and guide a drill bit.

5. The targeting guide of claim 1, wherein the second guide sleeve is configured to receive and guide a drill bit.

6. A targeting guide comprising:
a first guide sleeve defining a first longitudinal axis and configured to receive a surgical guide wire;
a second guide sleeve defining a second longitudinal axis and configured to receive and guide a drill bit;
an articulating arm including a first pair of linkages having a first end and a second end, the first end being hingeably connected to the first guide sleeve at a first hinge point and a second pair of linkages forming an outer joint configured so that its length between a nested hinged joint, it forms, and a second hinge point can be adjusted to change the first distance and thereby be arranged so as to operatively connect the first guide sleeve and the second guide sleeve;
wherein the first longitudinal axis and the second longitudinal axis intersect at a predetermined intersection point in space and form an intersecting angle, the intersection point being located at a first distance from the first guide sleeve and at a second distance from the second guide sleeve;
wherein actuating the first pair of parallel linkages and the second pair of parallel linkages changes the intersecting angle and the first distance while maintaining the same intersection point.

7. The targeting guide of claim 6, wherein each of the linkages in the second pair having a first end and a second end, the first end being hingeably connected to the second guide sleeve at a second hinge point.

8. The targeting guide of claim 7, wherein the second ends of the linkages in the first pair are arranged and hingeably connected to the second ends of the linkages in the second pair to form a pair of nested hinged joints that allow the two pairs of linkages to flex and form a flex angle of less than 180 degrees while keeping the two linkages in each pair to remain parallel to each other.

9. The targeting guide of claim 8, wherein one linkage from each pair are connected to form a first of the pair of nested hinged joints and another linkage from each pair are connected to form a second of the pair of nested hinged joints.

10. The targeting guide of claim 9, wherein the first of the pair of nested hinged joints is an inner joint and the second of the pair of nested hinged joints is an outer joint.

11. A targeting guide comprising:
a first guide sleeve defining a first longitudinal axis;
a second guide sleeve defining a second longitudinal axis;
an articulating arm including a first pair of parallel linkages having a first end and a second end, the first end being hingeably connected to the first guide sleeve at a first hinge point and a second pair of parallel linkages having a first end and a second end, the first end being hingeably connected to the second guide sleeve at a second hinge point such that the first and second linkages are arranged so as to operatively connect the first guide sleeve and the second guide sleeve wherein one of the linkages in the second pair forming an outer joint is configured so that its length between the nested hinged joint, it forms, and the second hinge point can be adjusted;
wherein the first longitudinal axis and the second longitudinal axis intersect at a predetermined intersection point in space and form an intersecting angle, the intersection point being located at a first distance from the first guide sleeve and at a second distance from the second guide sleeve;
wherein actuating the first pair of parallel linkages and the second pair of parallel linkages changes the intersecting angle by adjusting the second hinge point and the first distance while maintaining the same intersection point.

12. The targeting guide of claim 11, wherein the second ends of the linkages in the first pair are arranged and hingeably connected to the second ends of the linkages in the second pair to form a pair of nested hinged joints that allow the two pairs of linkages to flex and form a flex angle of less than 180 degrees while keeping the two linkages in each pair to remain parallel to each other.

13. The targeting guide of claim 12, wherein one linkage from each pair are connected to form a first of the pair of nested hinged joints and another linkage from each pair are connected to form a second of the pair of nested hinged joints.

14. The targeting guide of claim 13, wherein the first of the pair of nested hinged joints is an inner joint and the second of the pair of nested hinged joints is an outer joint.

15. The targeting guide of claim 11, wherein the first guide sleeve is configured to receive a surgical guide wire and the second guide sleeve is configured to receive and guide a drill bit.

* * * * *